US007303913B2

(12) United States Patent
Choi et al.

(10) Patent No.: US 7,303,913 B2
(45) Date of Patent: Dec. 4, 2007

(54) RAPID DIAGNOSTIC METHODS OF PESTE DES PETITS RUMINANTS USING RECOMBINANT NUCLEOCAPSID PROTEIN EXPRESSED IN INSECT CELLS AND MONOCLONAL ANTIBODY

(75) Inventors: Kang-Seuk Choi, Seoul (KR); Jin-Ju Nah, Anyang-si (KR); Young-Joon Ko, Anyang-si (KR); Nam-In Jo, Seoul (KR)

(73) Assignee: Republic of Korea (Management: Ministry of Agriculture and Forestry, National Veternary Research), Anyang-si (KR)

( * ) Notice: Subject to any disclaimer, the term of this patent is extended or adjusted under 35 U.S.C. 154(b) by 0 days.

(21) Appl. No.: 11/261,611

(22) Filed: Oct. 31, 2005

(65) Prior Publication Data

US 2006/0127952 A1 Jun. 15, 2006

(30) Foreign Application Priority Data

Nov. 5, 2004 (KR) ..................... 10-2004-0089816

(51) Int. Cl.
*C12N 5/06* (2006.01)
*C12Q 1/70* (2006.01)
*G01N 33/00* (2006.01)

(52) U.S. Cl. .......................... 435/326; 435/5; 435/7.92

(58) Field of Classification Search ..................... None
See application file for complete search history.

(56) References Cited

OTHER PUBLICATIONS

Choi et al, Monoclonal antibody-based competitive ELISA for simultaneous detection of rinderpest virus and peste des petits ruminants virus antibodies, Veterinary Microbiology, 2003, vol. 96, p. 1-16. (See IDS).*

Libeau et al., A competitive ELISA using anti-N monoclonal antibodies for specific detection of rinderpest antibodies in cattle and small ruminants, Veterinary Microbiology, 1992, vol. 31, p. 147-160.*

Sinnathamby et al., Immune responses in goats to recombinant hemagglutinin-neuraminidase glycoproteins of Peste des Petits ruminats virus: identification of a T cell determinant, Vaccine, 2001, vol. 19, p. 4816-4823.*

Singh et al., Development of a monoclonal antibody based aompetitive-ELISA for detection and titration of antibodies to peste des petits ruminants (PPR) virus, Veterinary Microbiology, 2004, vol. 98, p. 3-15.*

G. Libeau, "Development of a competitive ELISA for detecting antibodies to the peste des petits ruminants virus using a recombinant nucleoprotein", Research in Veterinary Science, (1995), 58, pp. 50-55.

K. Choi et al., "Monoclonal antibody-based competitive ELISA for simulatneous detection of rinderpest virus and pese des petits ruminants virus antibodies", Veterinary Microbiology 96, (2003), pp. 1-16.

T. Ismail et al., "Cloning and Expression of the Nucleoprotein of Peste des Petits Ruminants Virus in Baculovirus for Use in Serological Diagnosis", Virology 208, (1995), pp. 776-778.

* cited by examiner

*Primary Examiner*—Bruce R. Campell
*Assistant Examiner*—Sharon Hurt
(74) *Attorney, Agent, or Firm*—Sughrue Mion Pllc.

(57) ABSTRACT

The present invention relates to a diagnostic method of Peste des Petits Ruminants (PPR), a viral animal disease. More specifically, the invention relates to a new diagnostic method capable of detecting PPRV antibodies safely, simply and rapidly with recombinant Nucleocapsid (N) protein of PPR virus (PPRV) and specific monoclonal antibody against N protein from PPRV.

13 Claims, 12 Drawing Sheets

Figure 1A

```
1                                                                              60
ATG GCG ACT CTC CTC AAA AGC TTG GCA TTG TTC AAG AAG AAC AAA GAC AAA GCG CCG ACG
 M   A   T   L   L   K   S   L   A   L   F   K   K   N   K   D   K   A   P   T
                                                                              120
GCA TCA GGT TCA GGA GGG GCC ATC CGG GGG ATT AAG AAT GTT ATC ATA GTC CCG ATT CCC
 A   S   G   S   G   G   A   I   R   G   I   K   N   V   I   I   V   P   I   P
                                                                              180
GGA GAC TCA TCC ATC ATT ACC CGT TCA AGA TTG CTC GAC AGG CTT GTC AGA TTG GCC GGA
 G   D   S   S   I   I   T   R   S   R   L   L   D   R   L   V   R   L   A   G
                                                                              240
CAT CCA GAT ATC AAC GGG TCA AAG CTG ACC GGC GTG ATG ATC AGC ATG CTT TCT TTG TTC
 D   P   D   I   N   G   S   K   L   T   G   V   M   I   S   M   L   S   L   F
                                                                              300
CTA CAC TCA CCC GGG CAA CTC ATC CAG CGC ATC ACA GAT GAT CCA GAT GTC AGT ATC CGC
 V   H   S   P   G   Q   L   I   Q   R   I   T   D   D   P   D   V   S   I   R
                                                                              360
CTT GTT CAG CTC CTC CAA ACT ACT ACA TCT CAC TCC CCC TTC ACC TTT CCA TCA CCT GGT
 L   V   Q   V   V   Q   S   T   R   S   Q   S   G   L   T   F   A   S   R   G
                                                                              420
CCT GAT TTG CAC AAT GAG GCA GAC ATG TAT TTC TCA ACT GAA GGG TCC TCG AGT GGG AGC
 A   D   L   D   N   E   A   D   M   Y   F   S   T   E   G   S   S   S   G   S
                                                                              480
AAG AAA AGG ATC AAC TGG TTT GAG AAC AGG CAA ATA ATA GAC ATA GAA GTG CAG GAT GCG
 K   K   R   I   N   W   F   E   N   R   Q   E   I   I   D   I   E   V   Q   D   A
                                                                              540
GAA GAG TTC AAT ATG TTA TTA GCC TCC ATA CTG GCA CAA GTT TGG ATT CTC CTG GCC AAA
 E   E   F   N   M   L   L   A   S   I   L   A   Q   V   W   I   L   L   A   K
                                                                              600
GCC GTT ACC GCA CCC CAC ACT GCA GCT GAC TCA GAA TTG ACA AGG TGG GTT AAA TAC ACA
 A   V   T   A   P   D   T   A   A   D   S   E   L   R   R   W   V   K   Y   T
                                                                              660
CAA CAA AGA AGA GTC ATT GGG GAA TTT CGC CTT GAC AAA GGC TGG CTA GAT GCG GTC CGC
 Q   Q   R   R   V   I   G   E   F   R   L   D   K   G   W   L   D   A   V   R
                                                                              720
AAC ACC ATT CCA GAA CAT CTA TCA CTC CGG CGG TTC ATG GTA TCT CTT ATA CTT GAC ATC
 N   R   I   A   E   D   L   S   L   R   R   F   M   V   S   L   I   L   D   I
                                                                              780
AAA AGG ACC CCT GGC AAC AAG CCA AGG ATT GCA GAA ATG ATC TCT GAC ATT GAT AAC TAT
 K   R   T   P   G   N   K   P   R   I   A   E   M   I   C   D   I   D   N   Y
                                                                              840
ATT GTC GAA GGC GGG CTC GCC ACT TTC ATC CTT ACC ATC AAC TTT GCT ATT GAA ACC ATC
 I   V   E   G   G   L   A   T   F   I   L   T   I   K   F   G   I   E   T   M
```

Figure 1B

```
                                                                        900
TAT CCT CCA CTA CCT CTT CAC CAC TTT CCC CCC CAC TTC TCC ACT ATA CAA TCC TTC ATC
 Y   P   A   L   G   L   H   H   F   A   G   H   L   S   T   I   H   S   L   H
                                                                        960
AAT CTG TAT CAA CAG CTA GGC GAA GTT GCA CCC TAC ATG GTA ATT CTA GAG AAC TCA GTT
 N   L   Y   Q   Q   L   G   E   V   A   P   Y   M   V   I   L   E   N   S   V
                                                                        1020
CAG AAC AAG TTT AGT GCA GGA GCC TAT CCT CTT CTC TGG AGC TAT GCC ATC GGT GTT GGA
 Q   N   K   F   S   A   G   A   Y   P   L   L   W   S   Y   A   H   G   V   G
                                                                        1080
GTC GAG CTG GAG AAC TCA ATG GGG GGG TTG AAC TTT GGT AGA TCA TAT TTT GAC CCG GCT
 V   E   L   E   N   S   M   G   G   L   N   F   G   R   S   Y   F   D   P   A
                                                                        1140
TAT TTT CGT CTC GGA CAG CAG ATG GTC AGA AGA TCC CCA GGA AAG GTC AGC TCT GTA ATC
 Y   F   R   L   G   Q   Q   M   V   R   R   S   P   G   K   V   S   S   V   I
                                                                        1200
GCA GCT GAG CTC GGC ATC ACA GCA GAG GAA GCT AAA CTA GTC TCG GAA ATC GCC TCT CAG
 A   A   E   L   G   I   T   A   E   E   A   K   L   V   S   E   I   A   S   Q
                                                                        1260
ACT GCG GAC GAA AGG ACC CCT AGA CGG ACC GGG CCC AGA CAG GCG CAG CTT TCC TTC CTC
 T   A   D   E   R   T   P   R   R   T   G   P   R   Q   A   Q   L   S   F   L
                                                                        1320
CAG CAT AAA ATA CCA CAG CCA CAC TCA CAT CCA TCC CCC ACC ACC CAA CAA CTC AAA CCT
 Q   H   K   I   P   Q   P   H   S   H   P   S   P   T   T   Q   Q   L   K   P
                                                                        1380
GCG ACC CCA AAT GGG CCC CAC GAA AAG GAC AAA AAA CGA GCA CGC TCA GGA AGG CCA AGA
 A   T   P   N   G   P   H   E   K   D   K   K   R   A   R   S   G   R   P   R
                                                                        1440
GGA GCA ACC CCC GAC CAA CTG CTC CTG GAA ATC ATG CCT GAA GAC GAG GTC CCG CGA GGG
 G   A   T   P   D   Q   L   L   L   E   I   M   P   E   D   E   V   P   R   G
                                                                        1500
TCT GGA CAA AAC CCT CGT GAG GCT CAA CGA TCG GCC GAG GCA CTC TTT AGA CTG CAG GCC
 S   G   Q   N   P   R   E   A   Q   R   S   A   E   A   L   F   R   L   Q   A
                                                                        1560
ATC GCC AAG ATT CTA GAG GCC CAG GAG GAG GGA GAA GAC AAC AGT CAG ATA TAT AAC GAC
 M   A   K   I   L   E   G   Q   E   E   G   E   D   N   S   Q   I   Y   N   D
                           1578
                           AAG GAT CTC CTC ACC TGA
                            K   D   L   L   T   *
```

Figure 3

Figure 8
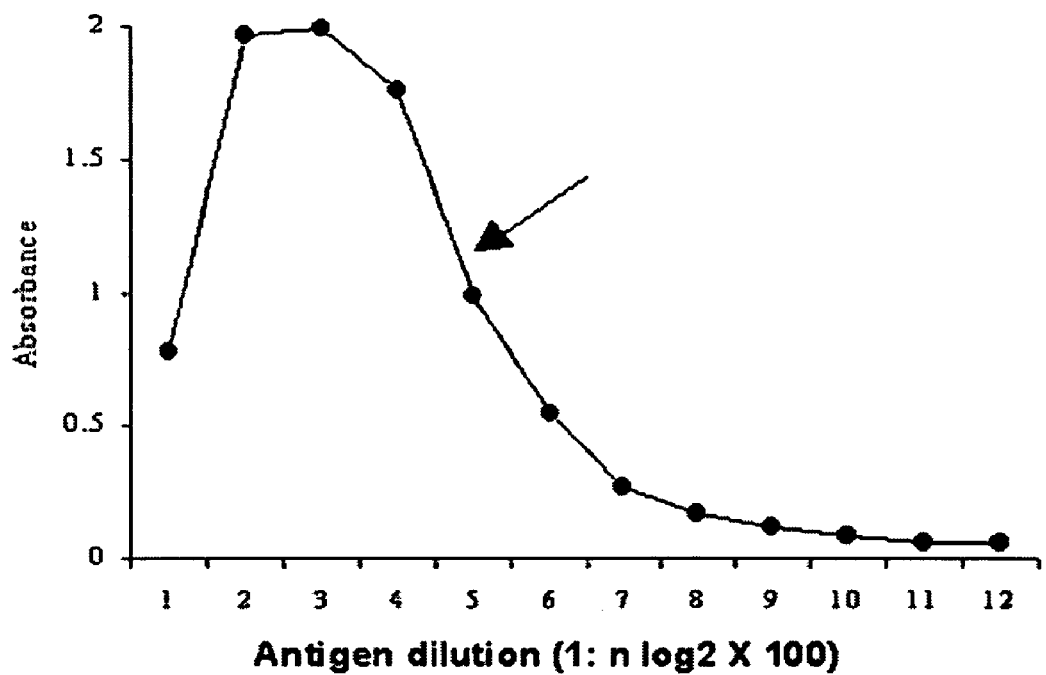
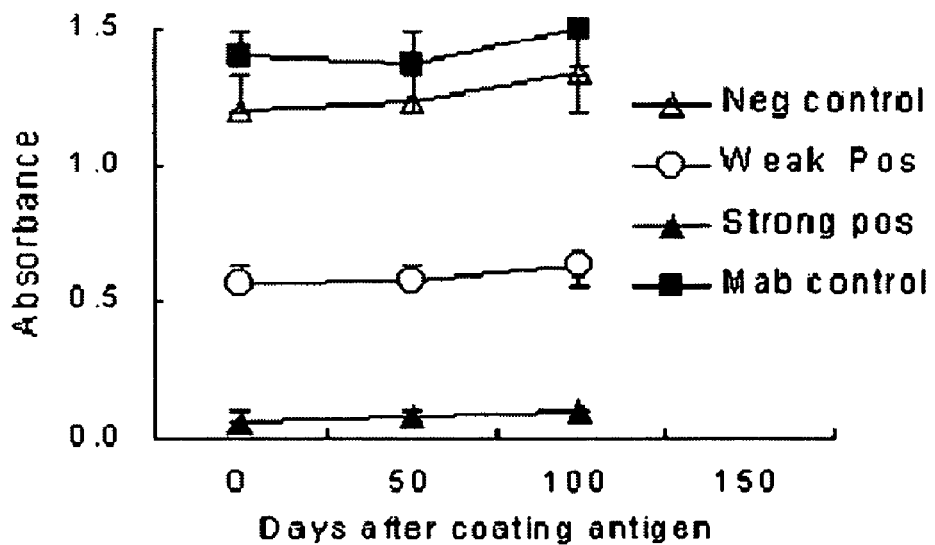

Figure 11

SEQUENCE LISTING

```
<160> NUMBER OF SEQ ID NOS: 3

<210> SEQ ID NO 1
<211> LENGTH: 1578
<212> TYPE: DNA
<213> ORGANISM: Peste-des-petits-ruminants virus

<400> SEQUENCE: 1
atggcgactc tcctcaaaag cttggcattg ttcaagaaga acaaagacaa agcgccgacg      60
gcatcaggtt caggaggggc catccggggg attaagaatg ttatcatagt cccgattccc     120
ggagactcat ccatcattac ccgttcaaga ttgctcgaca ggcttgtcag attggccgga     180
gatccagata tcaacgggtc aaagctgacc ggcgtgatga tcagcatgct ttctttgttc     240
gtagagtcac ccgggcaact gatccagcgg atcacagatg atccagatgt cagtatccgc     300
cttgttgagg tggtccaaag tactagatct cagtccgggt tgacctttgc atcacgtggt     360
gctgatttgg acaatgaggc agacatgtat ttctcaactg aagggtcctc gagtgggagc     420
aagaaaagga tcaactggtt tgagaacagg gaaataatag acatagaagt gcaggatgcg     480
gaagagttca atatgttatt agcctccata ctggcacaag tttggattct cctggccaaa     540
gcggttacgg caccggacac tgcagctgac tcagaattga gaaggtgggt taaatacaca     600
caacaaagaa gagtgattgg ggaatttcgc cttgacaaag ggtggctaga tgcggtccgc     660
aacaggattg cagaagatct atcactccgg cggttcatgg tatctcttat acttgacatc     720
aaaaggaccc ctggcaacaa gccaaggatt gcagaaatga tctgtgacat tgataactat     780
attgtcgaag ccgggctcgc cagtttcatc cttaccatca gtttggtat tgaaaccatg     840 tatcctgcac taggtcttca cgagtttgcc ggggagttgt ccactataga atccttgatg     900
aatctgtatc aacagctagg cgaagttgca ccctacatgg taattctaga gaactcagtt     960
cagaacaagt ttagtgcagg agcctatcct cttctctgga gctatgcgat gggtgttgga    1020
gtcgagctgg agaactcaat gggggggttg aactttggta gatcatattt tgacccggct    1080
tattttcgtc tcggacagga gatggtcaga agatccgcag gaaaggtcag ctctgtaatc    1140
gcagctgagc tcggcatcac agcagaggaa gctaaactag tctcggaaat cgcctctcag    1200
actggggacg aaaggaccgc tagagggacc gggcccagac aggcgcaggt ttccttcctc    1260
cagcataaaa taggagaggg agagtcacat gcatcggcga ccagggaaga agtcaaagct    1320 gcgacccaa atgggcccga cgaaaaggac aaaaaacgag cacgctcagg aaggccaaga    1380
ggaggaaccc ccgaccaact gctcctggaa atcatgcctg aagacgaggt cccgcgaggg    1440
```

-continued

```
tctggacaaa accctcgtga ggctcaacga tcggccgagg cactctttag actgcaggcc    1500
atggccaaga ttctagaggg ccaggaggag ggagaagaca acagtcagat atataacgac    1560
aaggatctcc tcagctga                                                  1578
```

<210> SEQ ID NO 2
<211> LENGTH: 28
<212> TYPE: DNA
<213> ORGANISM: Artificial Sequence
<220> FEATURE:
<223> OTHER INFORMATION: Forward primer

<400> SEQUENCE: 2
aaggcgccat ggcgactctc ctcaaaag                                       28

<210> SEQ ID NO 3
<211> LENGTH: 28
<212> TYPE: DNA
<213> ORGANISM: Artificial Sequence
<220> FEATURE:
<223> OTHER INFORMATION: Reverse primer

<400> SEQUENCE: 3
aagagctctc agctgaggag atccttgt                                       28

RAPID DIAGNOSTIC METHODS OF PESTE DES PETITS RUMINANTS USING RECOMBINANT NUCLEOCAPSID PROTEIN EXPRESSED IN INSECT CELLS AND MONOCLONAL ANTIBODY

FIELD OF THE INVENTION

The present invention relates to a diagnostic method for Peste des Petits Ruminants (PPR), a viral disease in animals, and provides the a new diagnostic method for PPRV using recombinant Nucleocapsid (N) protein, expressed in insect cells, and the specific monoclonal antibody against N protein from PPRV(Peste des Petits Ruminants Virus).

More specifically, the invention relates to a PPR diagnostic method using a one-step Reaction Enzyme-Linked ImmunoSorbent Assay (ELISA) that detects peroxidase labeled monoclonal antibody competing with serum antibodies for 30 minutes to bind to pre-coated recombinant N protein of PPRV on the ELISA plates.

BACKGROUND OF THE INVENTION

Peste des Petits Ruminants (PPR) is an infectious viral disease of ruminants including goats, sheep and cattle. Since PPR was first described in western Africa in 1942, it has become widely distributed in areas from south-Saharan desert regions in Africa and Middle east countries to southwest Asia, including Bangladesh.

Clinical signs include severe erosions in the mouth and lips, difficulty in breathing and diarrhea. Most deaths in affected animals result from severe diarrhea. PPR is one of the OIE list A diseases internationally and one of the obligatory notifiable animal diseases in Korea, because of its huge economic damage to the livestock industry of the countries in which it has occurred with very high morbidity and mortality in susceptible hosts. PPR is regarded as a foreign animal disease in Korea, since there has been no outbreak report so far.

Therefore, rapid detection by a rapid diagnostic test and destruction of PPR infected animals is very important to minimize the economic impact on the live stock industry.

PPR can be diagnosed by detection of viral antigen (antigen detection method) and by detection of antibodies from the infected animals (antibody detection method).

With regard to antigen detection methods; virus isolation and identification, reverse transcriptase-polymerase chain reaction (RT-PCR), and antigen detection ELISA have been applied, using tissue samples, pathological samples from mouth lesions and faeces from infected dead animals. However, these methods should be carried out in BL3 (biosafety level 3) laboratories.

As for antibody detection methods; virus neutralization test and ELISA have been applied for PPR diagnosis. The diagnostic method using ELISA can be performed general laboratories, whereas the virus neutralization test must be performed BL3 laboratories. For PPR diagnosis, inactivated viral particles, recombinant hemagglutinin(H) proteins or recombinant N proteins have been used for antigens in prior ELISA assays, and at least 3 hours has been required to perform the assays.

SUMMARY OF THE INVENTION

Therefore, the inventors recognized that the method using recombinant viral proteins would be the most effective method to perform in general laboratories for rapid diagnosis of PPR. The invention was accomplished by innovatively shortening the three or more steps of the former ELISA assays to a one-step ELISA that is able to detect PPR antibodies rapidly and precisely by using antigen coated ELISA plate and a peroxidase labeled monoclonal antibody.

In consequence, the purpose of this invention is to provide a new diagnostic method to detect PPRV antibodies by one-step reaction between antigen and test serum on antigen pre-coated plates.

To accomplish this purpose, the PPR antibody detection method of the invention has the characteristic that PPR antibodies in serum samples can be detected by one-step ELISA based on detection of bound peroxidase labeled monoclonal antibody following competition with serum antibodies on a plate pre-coated with recombinant N protein expressed in insect cells.

BRIEF DESCRIPTION OF THE DRAWINGS

FIGS. 1A and 1B represent the gene coding N protein of PPRV inserted into the expression vector, named pFastBac/PPRVN.

FIG. 3 represents the schematic figure of the recombinant expression vector, pFastBac/PPRVN containing full-length N gene of PPRV.

Lane M: Protein molecular size marker

Figure 6:
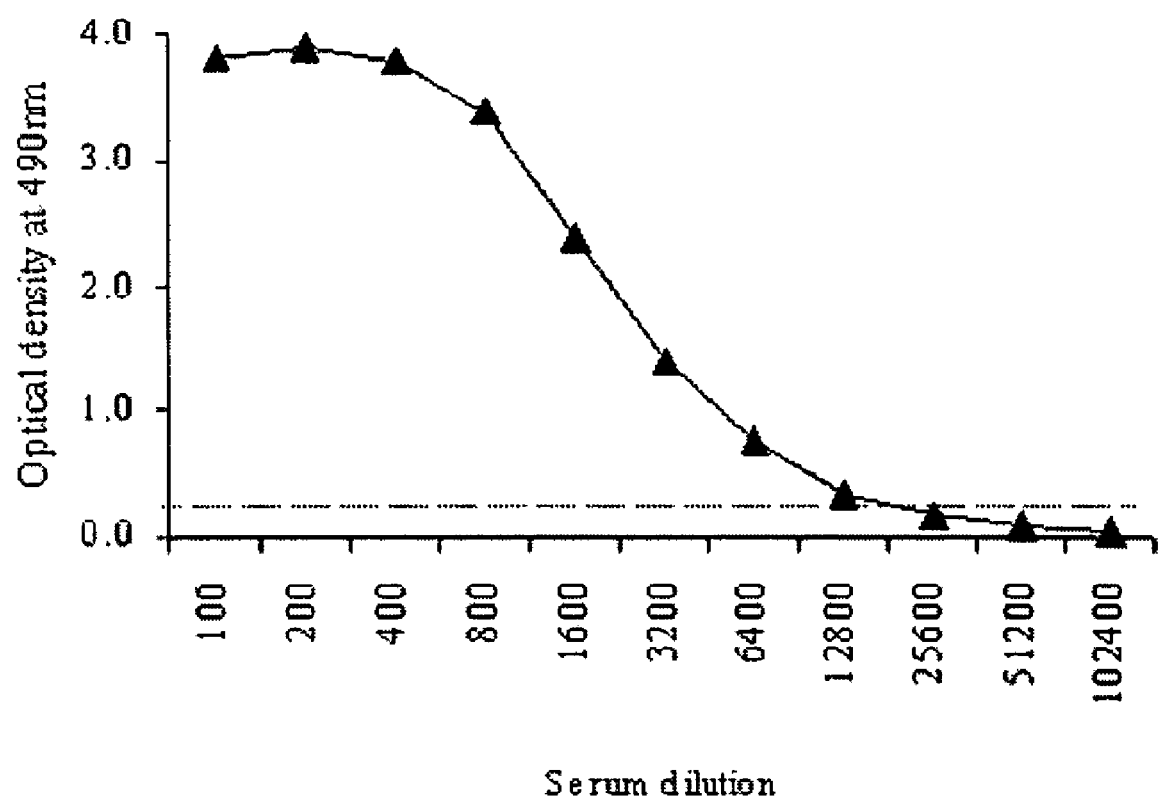

Lane 1: Result of detection of recombinant N protein using an N protein specific monoclonal antibody Lane 2: Result of recombinant N protein using a PPRV specific anti-serum FIG. 6 represents the concentration of recombinant N protein titrated by a monoclonal antibody based indirect ELISA.

Figure 7:
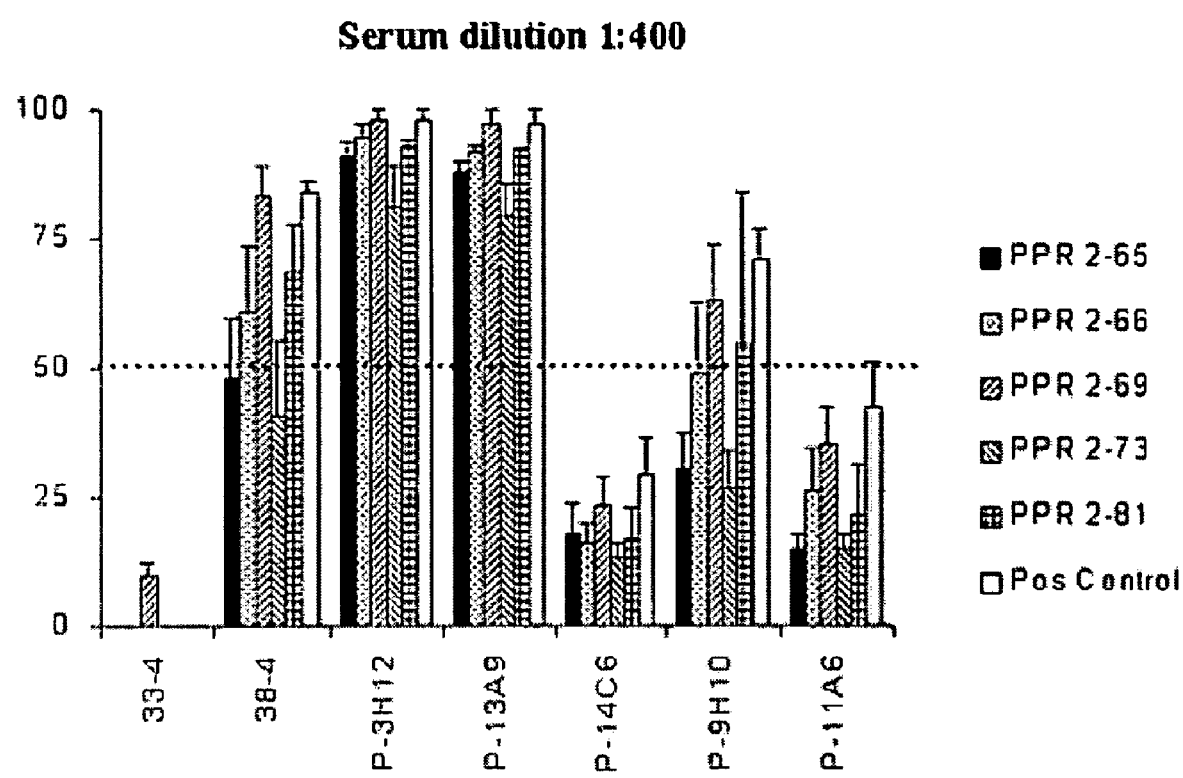

FIG. 7 represents immuno-dominant epitope on N protein of PPRV recognized by monoclonal antibody P-3H12.

PPR 2-65, 2-66, 2-69, 2-73 and 2-81: PPRV positive field sera

Pos Control: PPRV reference positive serum 33-4, 38-4, P-3H12, P-13A9, P-14C6, P-9H10 and P-11A6: monoclonal antibodies against N protein of PPRV FIG. 8A represents the optimal concentration of recombinant N protein for coating determined by indirect ELISA and FIG. 8B represents the stability of the N antigen.

Figure 9:
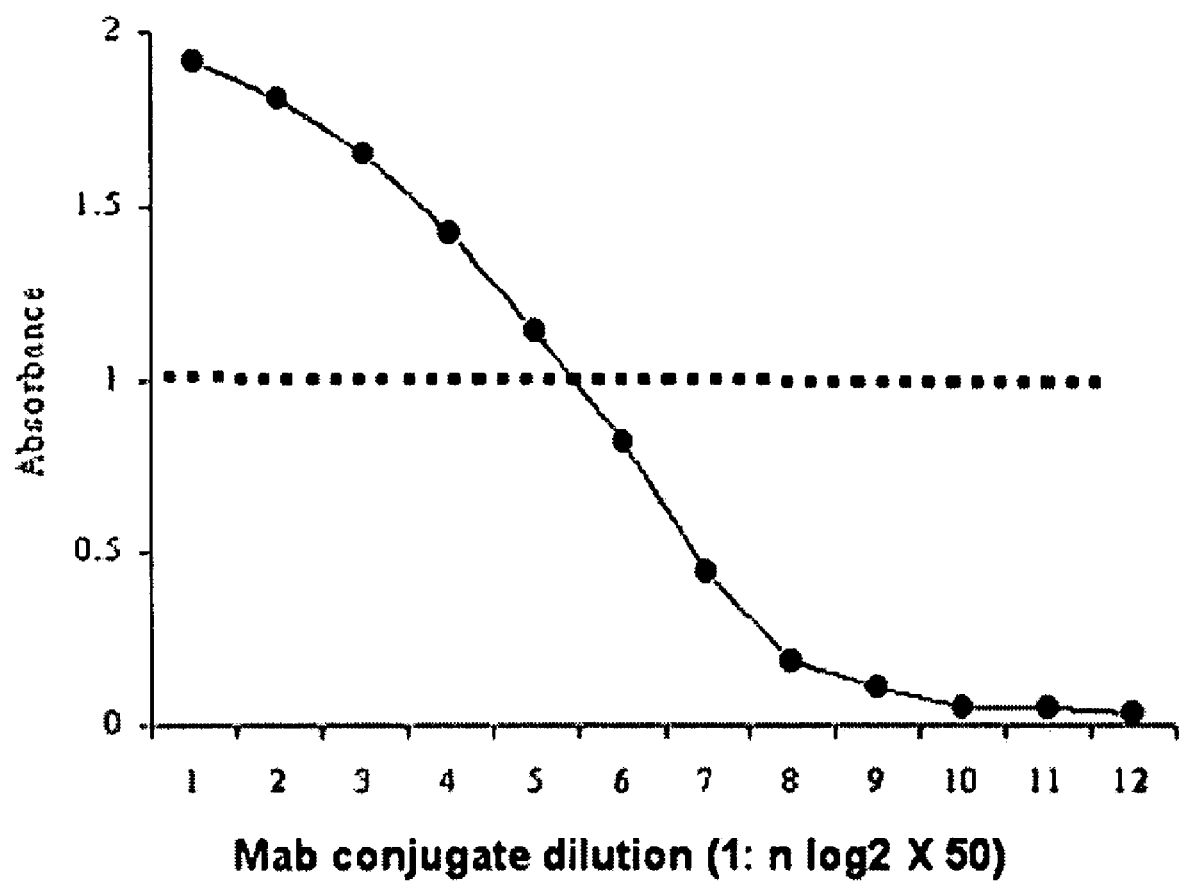

FIG. 9 represents the optimal concentration of the peroxidase conjugated monoclonal antibody P3-H12 determined by indirect ELISA.

Figure 10:
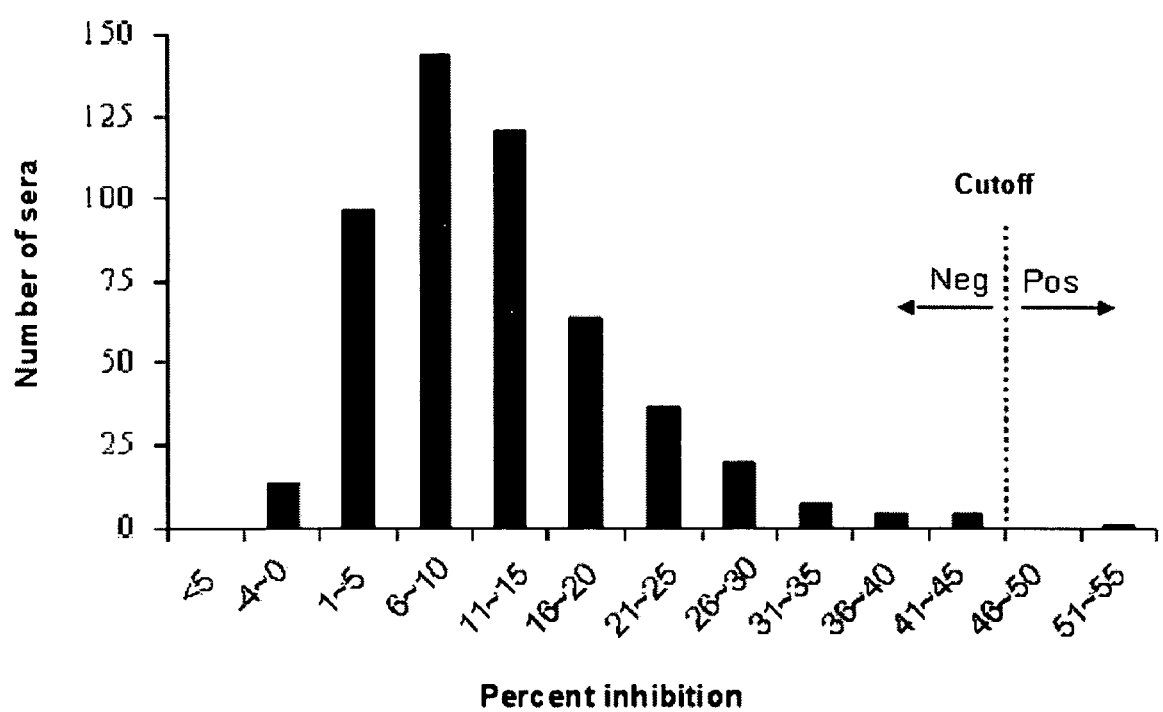

FIG. 10 represents the results of PPRV negative sera in one-step ELISA.

Figure 11:
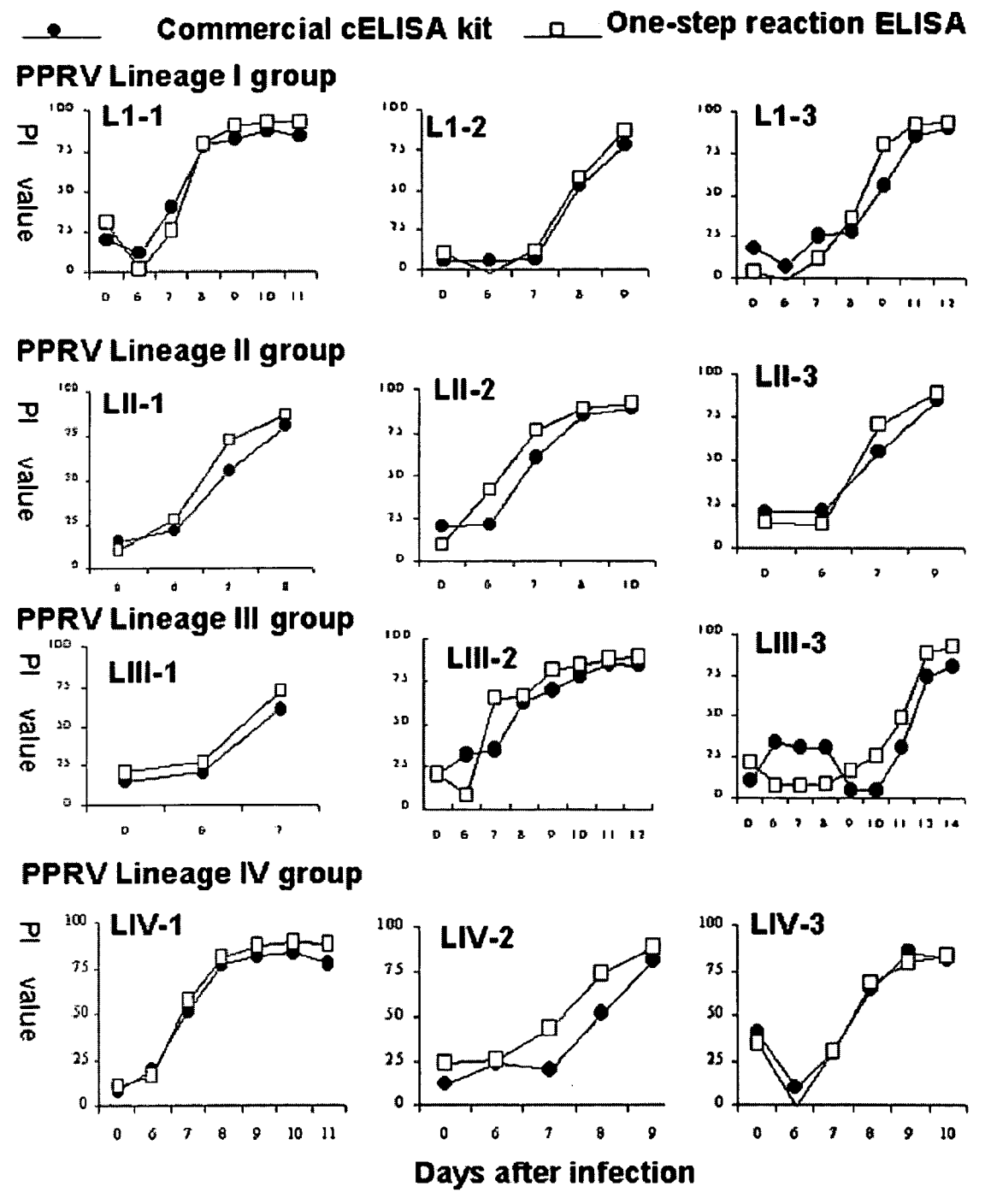

FIG. 11 represents the comparative results of one-step ELISA and a reference ELISA kit using PPRV infected goat sera.

DETAILED EXPLANATION OF THE INVENTION

Recombinant baculovirus (abbreviated as Bacmid/PPRVN) of the invention has characteristics as follows;

The Bacmid/PPRVN contains the gene coding N protein of PPRV and produces antigens for one-step ELISA. Unlike recombinant antigens of the former ELISA assays, the recombinant proteins of Bacmid/PPRVN have 6× Histidine bound to the amino-terminal of the proteins to facilitate easy identification of protein expression and purification.

N protein gene of PPRV of the invention is originated from PPRV Nigeria75/1 strain isolated in Nigeria (NCBI Genbank L39878, FIGS. 1A and 1B). The N protein with Molecular weight of 58 kDa consists of 525 amino acids. As the major protein forming nucleocapsid in host cells, N protein can induce strong humoral and cellular immunity because of the highest production among viral structural proteins in host cells.

In addition, P-3H12, N protein-specific monoclonal antibody of the invention, has the characteristics that it is originated from B lymphocytes of Balb/c mice immunized with PPR Nigeria 75/1 strain, it binds to an immunodominant epitope on PPRV N protein which induces strong immunity, and it functions as the detector in one-step ELISA. Moreover, the monoclonal antibody has another characteristic in that it can be used as peroxidase conjugated antibody for one-step ELISA.

The invention is explained more specifically as follows.

Figure 2:
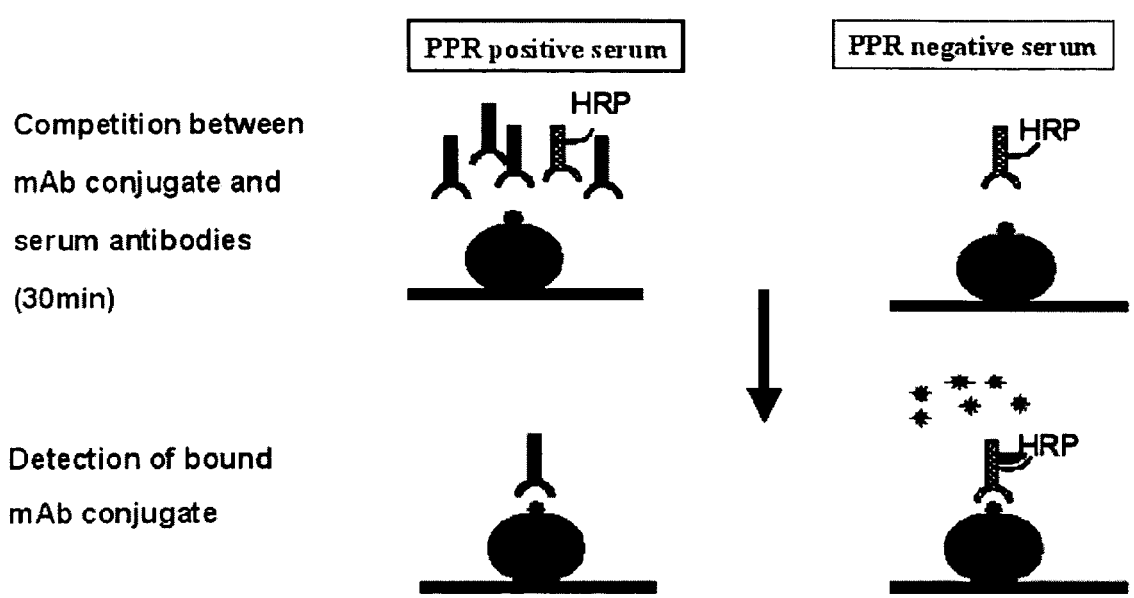
FIG. 2 represents the diagnostic scheme of the newly invented one-step ELISA.

ELISA assay for PPR diagnosis in the invention has the following steps:

(1) the reaction step having a competitive reaction between the conjugated monoclonal antibody and test sera on recombinant N protein-precoated ELISA plates;

(2) the washing step to remove unbound antibodies on the antigen coated plates;

(3) the reading step to calculate PPR antibody level in test sera by measuring optical density(OD);

and all of the steps are schematized in FIG. 2.

In addition, the ELISA assay of the invention includes two more steps; the preparation of ELISA plates pre-coated with recombinant N protein of PPR expressed in insect cells, and the preparation of monoclonal antibody conjugated to horseradish peroxidase. Procedures, reagents and reaction conditions related to the ELISA assay of the invention can be modified by broadly applied conventional methods in the industry.

The ELISA assay of the invention is excellent in its sensitivity and specificity because it uses the monoclonal antibody binding to the immuno-dominant epitope. It has another advantage in that it can detect rapidly any PPRV infection because amino acid sequences of the N protein are highly conserved among strains of PPRV.

The recombinant protein of the invention is expressed as fusion protein fused with 6× Histidines for easy identification of protein expression and purification. The recombinant N protein can be extracted from infected cells by conventional methods. In the invention, recombinant N proteins may be produced in insect cell expression systems after cloning of N protein gene and construction of the expression vector.

Production of recombinant N protein is not limited to the insect cell expression system, but also includes other recombinant protein expression systems, such as *E. coli*, adenovirus or yeast expression systems.

In addition, monoclonal antibody of the invention can be generally produced from hybridomas, in which mouse myelomas are fused with B lymphocytes from immunized mice with PPR viral antigen or recombinant N protein. Such hybridoma can be produced by conventional methods in the industry, such as the HAT selection method. It is possible to select some hybridomas with high affinity to N protein and reaction on immuno-dominant epitopes on N protein among various hybridomas producing monoclonal antibodies; for example, a hybridoma cell line deposited in Korean Cell Line Research, Seoul, Korea (deposit number KCLRF-BP-00104) is available.

The invention will be specified in detail in the following examples and tests. However, the invention is not restricted by such examples, and may also include any conventional modification, substitution, and insertion in the industry in the range of the invention.

PREFERRED EMBODIMENT OF THE INVENTION

EXAMPLE 1

Genomic RNA Extraction from PPRV-Infected Cells

PPR virus Nigeria75/1 strain, isolated from a goat in Nigeria in 1975 and supplied by CIRAD-EMVT, France, was inoculated into VERO (ATCC CCL81, USA) cells, then viral genome was extracted from the cell culture supernatant using RNeasy RNA extraction kit (Qiagen, USA) according to the manufacturer's instructions.

EXAMPLE 2 cDNA Synthesis and Cloning of N Gene of PPR Virus

Complementary DNA of full-length N gene of PPR virus was synthesized by RT premix kit (bioneer, R.O.Korea) using genomic RNA (see example 1) and a primer 2 (reverse primer) below. The synthesized DNA was PCR-amplified by a PCR premix kit (Bioneer, Korea) using primers 1 and 2 below. The PCR amplication was carried out under conditions of pre-denaturation (10 min at 95° C.), a 30-cycle PCR reaction (denaturation for 60 sec at 94° C.; annealing for 60 sec at 58° C.; and extension for 60 sec at 72° C.), and final ligation (5 min at 72° C.) using a PCR machine (PE9600, Perkin Elmer). The primers were designed based on the published N gene sequence of PPR virus Nigeria 75/1 (Genbank accession number L39878) as follows:

```
Primer 1 (Forward primer):
5'-AAGGCGCCATGGCGACTCTCCTCAAAAG-3'

Primer 2 (Reverse primer):
5'-AAGAGCTCTCAGCTGAGGAGATCCTTGT-3'
```

Restriction enzyme sites (Nar1 site for primer 1 and Sac1 site for primer 2) were incorporated at the 5' ends of each primer to facilitate cloning as indicated by the underlined nucleotides. Resulting DNA product amplified above was inserted into pGEM-Teasy vector (Promega, USA) to generate recombinant plasmid "pGEM/PPRVN". Proper orientation of the insert was confirmed by the dideoxynucleotide chain termination sequencing method using the ABI Model 373A DNA sequencer (Applied Biosystem, USA) by comparison with the sequence of the N gene of PPR virus shown in FIGS. 1A and 1B.

EXAMPLE 3

Construction of Recombinant Expression Vector Encoding N Gene of PPR Virus

Figure 3:
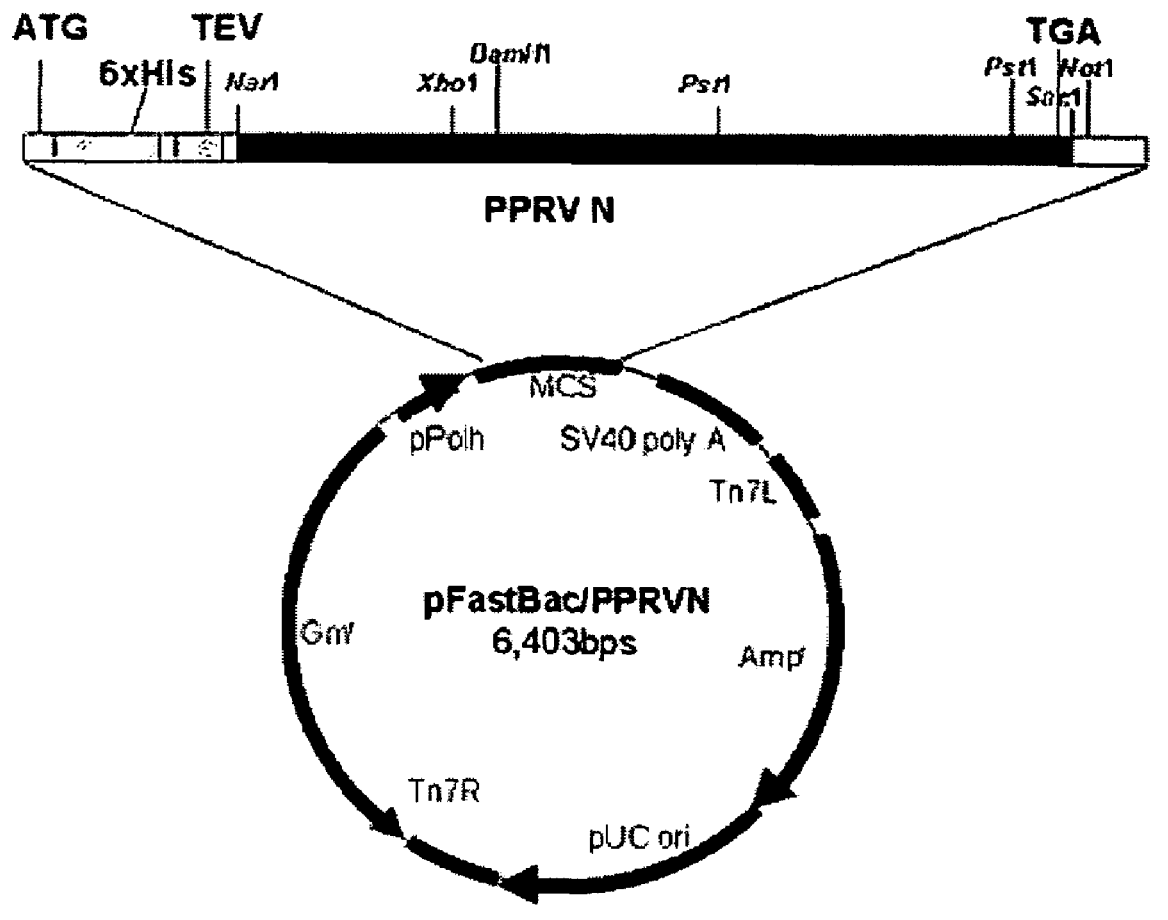

DNA fragment of 1,587 bps, extracted from the pGEm/PPRVN, was inserted into the Nar1 and Sac1 restriction enzyme sites of pFastBac HT vector (Invitrogen, USA), which were designed to express fusion protein with 6× His. Resulting recombinant plasmid with PPRV N gene was designated "pFastBac/PPRV-N", as shown in FIG. 3.

EXAMPLE 4

Generation of Recombinant Baculovirus Expressing N Protein of PPRV

Figure 4:
FIG. 4 represents a picture showing that expressed recombinant N protein of PPRV was confirmed by a monoclonal antibody against N protein.
Figure 5:
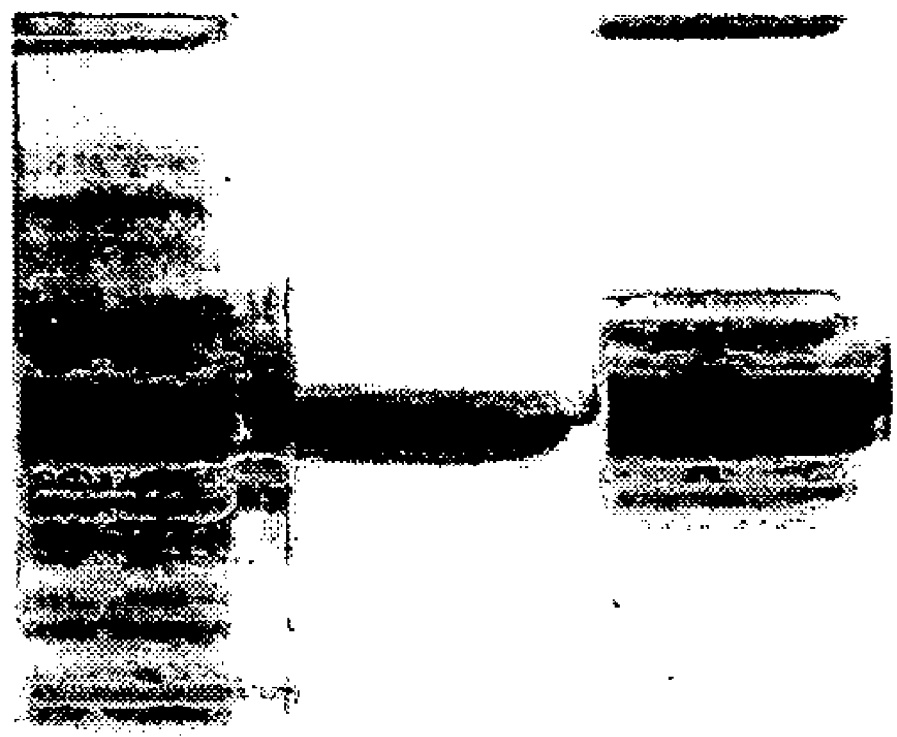
FIG. 5 represents detection of expressed recombinant N protein of PPRV in Western blot.

Recombinant baculovirus Bacmid/PPRVN was generated using a commercialized Baculovirus expression system (Invitrogen, USA). For this purpose, recombinant baculovirus DNA, Bacmid/PPRVN DNA was constructed by transforming expression vector pFastBac/PPRVN (see Example 3) into *E. coli* DH10Bac cells. The mixture of Bacmid/PPRVN DNA (5 µg in 100 µl serum-free Grace's medium) and Cellfectin (Invitrogen) (6 µl in 100 µl serum-free Grace's medium) was incubated at room temperature for 30 min. During the incubation, *Spodoptera frugiperda*(S-f21) cell monolayer (GibcoBRL, $2 \times 10^6$ cells in well of 35 nm cell culture petridish) was washed using serum-free Grace's medium. The mixture was then co-transfected into the S-f21 cells for 5 hrs at 27° C. After incubation, the mixture solution was replaced with 2 ml volume of fresh Grace's medium containing 10% fetal bovine serum. The cells were incubated for 4 to 6 days at 27° C. until cytopathic effects were observed. Cell culture supernatant containing recombinant baculoviruses was harvested to purify recombinant baculoviruses by using plaque assay. Briefly, a 100 µl volume of recombinant baculoviruses harvested was inoculated onto a monolayer of S-f21 cells ($2 \times 10^6$ in well of 35 mm petridish) for 1 hr at 27° C. The cell monolayer was overlaid using Grace's medium containing 1.5% low-melting agarose for 3 to 4 days of incubation at 27° C. to pick up plaque containing recombinant virus. The plaques were infected into fresh S-f21 cells for 3 to 4 days. Cells showing cytopathic effects were examined in indirect immunofluorescence assay and Western blot using PPRV-specific monoclonal antibody to select recombinant baculovirus Bacmid/PPRVN expressing PPR N protein. FIG. 4 describes the result of detection of recombinant N protein expressed in baculovirus-infected cells in immunofluorescence assay using PPRV-specific monoclonal antibody. FIG. 5 describes the result of detection of recombinant N protein expressed in baculovirus-infected cells in Western blot using PPRV-specific monoclonal antibody and PPR positive serum.

EXAMPLE 5

Recombinant N Protein Antigen and Preparation of N Protein-Coated ELISA Plates

Recombinant N protein of PPRV (rPPRV-N) was prepared in insect cells infected with a recombinant baculovirus (Bacmid/PPRV-N) expressing PPRV N protein. Briefly, the S-f21 cells in a 175 cm² tissue culture flask were infected with the recombinant baculovirus (Bacmid/PPRV-N) at a multiplicity of infection of 0.1. After 90 min incubation at 27° C., the infected cells were removed from the flask and then added into 200-ml S-f21 cell culture ($2 \times 10^6$/ml) of a spinner culture vessel. The infected cells in the spinner culture vessel were incubated for 4 or 5 days at 27° C., then the cells were harvested from the culture vessel. After centrifugation at 500×g for 20 min at 4° C., the cells were collected and resuspended in 1/20 volume of a lysis buffer (0.01 M phosphate buffered saline containing 1% Triton X-100) containing protease inhibitor cocktail (Roche Molecular Biochemicals, Germany). After 5 min incubation at room temperature, the cell lysates were sonicated to extract the recombinant N protein. Finally, the lysate was clarified by centrifugation at 500×g for 20 min at 4° C. and the supernatant was used as an ELISA antigen.

FIG. 6 describes the result of quantification of the above prepared ELISA antigen in indirect ELISA using monoclonal antibody P-3H12 (see Example 6). As shown in FIG. 6, the PPRV N antigen was reactive (OD>0.2) even at 1:12800 dilution when measured by indirect ELISA using monoclonal antibody P-3H12.

EXAMPLE 6

Generation of Hybridoma Producing PPRV-Specific Monoclonal Antibody

Semi-purified PPRV (Nigeria75/1, CIRAD-EMVT, France) was used to produce monoclonal antibody. Briefly, PPRV-infected Vero cells were harvested and frozen-thawed three times. The resulting lysates were clarified by centrifugation at 5000×g for 30 min. Polyethylene glycol 800 (23 g/l) and sodium chloride (70 g/l) were added to the supernatant containing PPRV and left overnight at 4° C.

The aggregated PPRV was precipitated by centrifugation at 5000×g for 30 min and the pellets were resuspended in 10 ml of 0.01M PBS. The concentrated PPRV were semi-purified by using 25% (w/v) Sucrose-gradient ultracentrifugation at 100,000×g for 90 min. The PPRV was quantified using GenQuanll (Pharmacia Biotech, USA) to adjust to 0.1 mg/ml.

BALB/c mice were immunized with purified viral antigen (50 µg per dose in Freund's incomplete adjuvant) via foot-pad route. Ten to fifteen days after immunization, the lymphocytes derived from popliteal lymph nodes of immunized mice were harvested and fused with the SP2/0-Ag14 myeloma cells using polyethylene glycol 1500 (Boehringer Mannheim, Germany) by the conventional method. Briefly, popliteal lymphocytes were washed with serum-free medium (SFM) and mixed with SP2/0-Ag14 mouse myeloma cells at a ratio of 5:1 to 10:1. One ml of PEG1500 solution was added to the mixture of lymphocytes and myeloma cells. PEG-mediated fusion cells were diluted in HAT(Hypoxanthine Aminopterin Thymidine) medium containing 10% fetal bovine serum and distributed into 96 wells (100 µl per well) of tissue culture microplates, which had previously been cultured with mouse peritoneal macrophage cells. The plates were incubated in a $CO_2$ incubator at 37° C. Hybridoma cells secreting N protein of PPRV monoclonal antibody were screened by indirect ELISA using recombinant N protein (see Example 5). The positive hybridoma cells were subjected to cloning by the limiting dilution method, and finally inoculated intraperitoneally into BALB/c mice, which were primed by Freund's incomplete adjuvant. Ascitic fluid was collected 1 to 2 weeks later.

Characteristics of monoclonal antibody selected are shown in Table 1.

TABLE 1

| Characterization of monoclonal antibody specific for PPRV N protein produced in Example 6. | | | |
|---|---|---|---|
| Monoclonal antibody (hybridoma) | Immunogen | Isotype | Target protein |
| P-3H12 | PPRV | IgG2a, κ | N protein |
| P-13A9 | PPRV | IgG2b, κ | N protein |
| P-9H10 | PPRV | IgG1, κ | N protein |
| P-11A6 | PPRV | IgG2b, κ | N protein |
| P-14C6 | PPRV | IgM, κ | N protein |

EXAMPLE 7

Selection of Monoclonal Antibody P-3H12 for One-Step ELISA

A competitive ELISA was carried out to select monoclonal antibody for one-step ELISA using recombinant N protein antigen (see Example 5) and monoclonal antibodies (see Example 6). Maxisorp™ ELISA plates (Nunc, Denmark) were coated with 50 µl of purified PPRV antigen (1:1500 dilution in 0.01M PBS) for 1 hour at 37° C. After washing three times with wash buffer (0.002 M PBS containing 0.05% polysorbate 20 (Tween® 20), 25 µl of optimally diluted monoclonal antibody and each test serum at a 1:400 dilution in blocking buffer (PBS containing 0.5% bovine serum and 0.05% polysorbate 20 (Tween® 20) were added to duplicate wells. Reference positive and negative serum controls were included in each plate. After a 1-hour incubation at 37° C. with shaking, the plates were washed three times and incubated at 37° C. for 1 hour with peroxidase-labeled anti-mouse immunoglobulins (Kirkegaard-Perry Laboratories, Inc., 50 µl per well) diluted 1:2000 in blocking buffer. Following another washing step, the plates were incubated for 10 mm with the substrate O-phenylenediamine (Sigma, USA) in 0.05M citrate phosphate buffer (pH 5.0). Colormetric reaction was stopped by adding 50 µl volume of 1.25 M sulfuric acid to all wells. Optical density (OD) readings were measured at the 492 nm wavelength. The reaction was considered as competition positive when the OD of the monoclonal antibody in the presence of test serum showed a 50% or greater reduction of that of the monoclonal antibody alone. FIG. 7 shows comparative immunogenic activity of each epitope recognized by each monoclonal antibody in competitive ELISA. Monoclonal antibodies 33-4 and 38-4 against PPRV Nigeria75/3 strain were used as control monoclonal antibodies, and the remaining five monoclonal antibodies were produced as above (see Example 6). As shown in FIG. 7, an epitope recognized by monoclonal antibody P-3H12 was the most immunogenic. Hybridoma secreting monoclonal antibody P-3H12 was deposited in Korean Cell Line Research on Oct. 11, 2004 (Deposit No. KCLRF-BP-00104) at the Korean Cell Line Research Foundation, Cancer Research Institute, Seoul National University College of Medicine, 28 Yongon-dong, Chongno-Gu, Seoul, 110-744, Republic of Korea.

EXAMPLE 8

Preparation of ELISA Plates Coated with Recombinant N Proteins

Recombinant N proteins prepared as the above Example 5 were added 50 ul/well diluted 1500-fold in 0.01M PBS onto ELISA plates (Maxisorp, Nunc) and incubated at 37° C. for 1 hour. After incubation the plates were washed three times with 0.01M PBS to remove the unreacted remnants. Protein stabilization solution (Sigma, USA) was added to block the unreacted sites on the plates and incubated at room temperature for 1 hour, and the plates were dried and stored at 4° C. until use. Optimal concentration of recombinant N protein was determined by indirect ELISA as shown in FIG. 8A. FIG. 8B shows the stability of the coated N protein evaluated with standard anti-PPRV serum on incubation at 4° C. As shown in FIG. 8B, the coated N protein was stable for at least 100 days without losing the antigenic activity.

EXAMPLE 9

Conjugation of Monoclonal Antibody (P-3H12) to Horseradish Peroxidase

Monoclonal antibody (P-3H12) was purified according to the manufacturer's protocol. The purified monoclonal antibody was conjugated to peroxidase using peroxidase labeling kit (Roche,USA). The conjugated monoclonal antibody was mixed with the stablilization solution supplied within the kit, frozen under liquid nitrogen, and stored at −70° C. FIG. 9 shows that the peroxidase-conjugated monoclonal antibody was quantified by indirect ELISA using the N protein-coated plates as in Example 8. As shown in FIG. 9, the optimal concentration of the conjugated monoclonal antibody was determined as 1:400 dilution of the conjugate for this ELISA.

EXAMPLE 10

One-Step ELISA for Diagnosis of PPR

One-step ELISA for diagnosis of PPR uses recombinant N protein-coated plates and peroxidase-conjugated monoclonal antibody, and the process is as follows. The N protein-coated plates were incubated with peroxidase-conjugated monoclonal antibody diluted 400-fold in blocking solution and an equal volume of sera diluted 10-fold in blocking solution at 37° C. for 30 min. After incubation, the plates were washed three times with PBST and developed with OPD (O-PhenyleneDiamine) solution at room temperature for 10 min. The reaction was stopped by adding 50 ul of 1.25M sulfuric acid and optical density was measured at 490 nm. The serum is determined positive if the percent inhibition (PI) is above 50% as compared to the control (containing peroxidase-conjugated monoclonal antibody only).

EXPERIMENTAL EXAMPLE 1

The Application of One-Step ELISA for PPR-Negative Ruminant Sera

The ELISA was performed with sera collected from domestic cattle and goats (n=510) that proved negative for PPR. FIG. 10 shows the results of the one-step ELISA for these sera. Of 510 sera, 508 sera proved negative, the specificity being 99.6%.

EXPERIMENTAL EXAMPLE 2

The Application of One-Step ELISA for Goat PPR-Positive Sera

The one-step ELISA was conducted for sera derived from goat infected with four lineages of PPRVs (3 goats per each lineage of PPRV). The results were compared to the standard ELISA recommended by FAO and OIE. FIG. 11 shows the results of one-step ELISA for goat PPR-positive sera. The one-step ELISA detected antibodies to PPRV not less than the standard ELISA, indicating its high sensitivity.

INDUSTRIAL APPLICABILITY

As shown in the above, the one-step ELISA curtailed the process dramatically as compared to the standard ELISA without losing sensitivity and specificity. The use of monoclonal antibody reactive to the immunodominant epitope of PPRV ensures the efficient detection of antibodies to PPRV. In addition, the short turnaround time and simple process of the one-step ELISA enables sera surveillance for PPR on a large scale. As PPR causes severe damage to the livestock industry in many African and Asian countries, if H or F structural protein were to be used as a vaccine, the one-step ELISA should be useful in differentiating infected from vaccinated animals.

What is claimed is:

1. A method for detecting a Peste des Petits Ruminants virus (PPRV) N-protein antibody in a sample comprising
   (a) providing a surface which is coated with an N-protein of PPRV;
   (b) contacting the surface with a labeled PPRV N protein antibody, said labeled PPRV N protein antibody being produced by a hybridoma P3H12 (KCLRF-BP-00104), wherein the contact of the surface and the labeled PPRV N protein antibody is carried out in the presence of the sample that contains the PPRV N protein antibody, and in the absence of the sample that contains the PPRV N protein antibody, respectively;
   (c) assaying to determine the quantity of the labeled PPRV N protein antibody bound to the surface, each in the presence of the sample that contains the PPRV N protein antibody, or in the absence of the sample that contains the PPRV N protein antibody; and
   (d) comparing the quantity of the labeled PPRV N protein antibody bound to the surface in the presence of the sample with the quantity of the labeled PPRV N protein antibody bound to the surface in the absence of the sample,
   wherein said N-protein of PPRV is a recombinant protein produced by expressing a recombinant baculovirus plasmid harboring the PPRV N-protein in an insect cell, said recombinant baculovirus plasmid having Nar1 and Sac1 restriction sites.

2. Hybridoma cell line(KCLRF-BP-00104), which is produced by fusing myeloma cells and immune cells derived from mouse infected with PPRV (Nigeria75/1 strain).

3. Monoclonal antibody, which is secreted by the hybridoma cell line according to claim 2.

4. The method for diagnosing Peste des Petits Ruminants according to claim 1, wherein the ELISA utilizes the monoclonal antibody secreted by the hybridoma cell line (KCLRF-BP-00104).

5. The method for diagnosing Peste des Petits Ruminants according to claim 4, wherein the ELISA utilizes the monoclonal antibody conjugated with peroxidase.

6. A method according to claim 1, wherein the contact of the surface and labeled PPRV N protein antibody in the presence of the sample that contains the PPRV N protein antibody is performed by contacting the surface with the sample which is suspected of containing the anti-PPRV antibody, followed by washing the surface to remove unbound anti-PPRV antibody.

7. A method according to claim 6, wherein the washing is performed using about 0.002M PBS containing about 0.05% polysorbate 20.

8. A method according to claim 1, wherein the label is a peroxidase.

9. A method according to claim 1, wherein the contacting the surface which is coated with an N-protein of PPRV with the labeled PPRV N protein antibody is performed at a temperature of about 37° C. for about 30 minutes.

10. A method according to claim 7, wherein the assaying to determine the quantity of the labeled PPRV N protein antibody of step (c) is performed by contacting the labeled PPRV N protein antibody with O-phenylenediamine for about 10 minutes.

11. A method according to claim 10, further comprising neutralizing a reaction mixture of the labeled anti-PPRV N protein antibody and O-phenylenediamine with sulfuric acid.

12. A method according to claim 1, wherein said surface is pre-coated.

13. A method according to claim 1, wherein said PPRV N protein is tagged with six histidines at its N-terminus.

* * * * *